United States Patent [19]
Schneider et al.

[11] Patent Number: 5,516,410
[45] Date of Patent: May 14, 1996

[54] PLANAR SENSOR ELEMENT HAVING A SOLID ELECTROLYTE SUBSTRATE

[75] Inventors: Gerhard Schneider, Vaihingen; Frank Westphal, Stegaurach; Margret Schuele, Markgröningen, all of Germany

[73] Assignee: Robert Bosch GmbH, Stuttgart-Feuerbach, Germany

[21] Appl. No.: 357,233

[22] Filed: Dec. 9, 1994

[30] Foreign Application Priority Data

Dec. 17, 1993 [DE] Germany .................... 43 43 089.9

[51] Int. Cl.$^6$ ................................................. G01N 27/26
[52] U.S. Cl. ............................................ 204/426; 204/408
[58] Field of Search .................................. 204/424, 425, 204/426, 427, 428, 429, 408

[56] References Cited

U.S. PATENT DOCUMENTS

| | | | |
|---|---|---|---|
| 4,579,643 | 4/1986 | Mase et al. | 204/427 |
| 4,610,741 | 9/1986 | Mase et al. | 204/424 |
| 4,645,572 | 2/1987 | Nishizawa et al. | 204/406 |
| 4,647,364 | 3/1987 | Mase et al. | 204/427 |
| 4,755,274 | 7/1988 | Mase et al. | 204/427 |
| 4,772,376 | 9/1988 | Yukawa et al. | 204/410 |
| 4,832,818 | 5/1989 | Sekido et al. | 204/426 |
| 4,839,018 | 6/1989 | Yamada et al. | 204/425 |
| 4,909,922 | 3/1990 | Kato et al. | 204/406 |
| 5,098,549 | 3/1992 | Friese et al. | 204/425 |
| 5,160,598 | 11/1992 | Sawada et al. | 204/429 |
| 5,164,068 | 11/1992 | Udo et al. | 204/424 |
| 5,169,512 | 12/1992 | Wiedenmann et al. | 204/426 |
| 5,298,147 | 3/1994 | Nakae et al. | 204/426 |

FOREIGN PATENT DOCUMENTS

| | | |
|---|---|---|
| 0142992 | 5/1985 | European Pat. Off. . |
| 0142993 | 5/1985 | European Pat. Off. . |
| 0194082 | 9/1986 | European Pat. Off. . |
| 0227257 | 7/1987 | European Pat. Off. . |
| 0259175 | 3/1988 | European Pat. Off. . |
| 2194846 | 3/1988 | United Kingdom . |

*Primary Examiner*—Bruce F. Bell
*Attorney, Agent, or Firm*—Spencer & Frank

[57] ABSTRACT

The invention is based on a planar sensor element for determining the oxygen content of gas mixtures, particularly in internal combustion engines such as those found in automobiles. The sensor element comprises a measuring cell and an integrated heat conductor embedded in electric insulation all of which rest on a solid electrolyte substrate. At least one hollow chamber separates one or several parts of the insulation from the solid electrolyte substrate in order to effect an improved decoupling of the sensor's heat conductor from its measuring cell.

10 Claims, 2 Drawing Sheets

PLANAR SENSOR ELEMENT HAVING A SOLID ELECTROLYTE SUBSTRATE

CROSS REFERENCE TO RELATED APPLICATION

This application claims the priority of German Application No. P 43 43 089.9 filed Dec. 17, 1993, which is incorporated herein by reference.

BACKGROUND OF THE INVENTION

The invention is based on a planar sensor element for determining the oxygen content of gas mixtures. The sensor element comprises an integrated heat conductor embedded in electric insulation resting on a solid electrolyte substrate. Sensor elements of this type are used in electrochemical measuring sensors and probes, such as those used to determine the oxygen content of gases and the λ value (total oxygen over oxygen required for complete fuel combustion) of gas mixtures, particularly in internal combustion engines.

Planar sensor elements have proven advantageous in practice because of a simple and cost-effective method of production involving the use of wafer- or film-shaped solid electrolytes, that is, ion-conductive materials such as stabilized zirconium dioxide. Planar polarographic sensor elements and probes that operate according to the diffusion resistance principle have achieved particular significance in practice. Sensor elements and probes of this type are known, for example, from German Published, Non-Examined Patent Applications 3,543,759 corresponding to U.S. Pat. No. 4,839,018 and U.S. Pat. No. 5,098,549, and 3,728,618, as well as from European Patent Applications 0,142,992, 0,142,993, and 0,194,082, and also from European Patent Application 0,148,622 corresponding to U.S. Pat. No. 4,610,741.

In polarographic probes of this type, which operate according to the diffusion resistance principle, the diffusion current at a constant voltage present at the two electrodes of the probe, or the limiting diffusion current can be measured. In an exhaust gas produced during combustion processes, the limiting diffusion current is a function of the oxygen concentration for as long as the diffusion of the gas toward the pumping electrode determines the rate of the occurring reaction. It is known to construct such polarographic probes, which operate according to the polarographic measuring principle, in such a way that both the anode and cathode are subjected to the gas to be measured, with the cathode exhibiting a diffusion barrier.

In their preferred embodiments, the known electrochemical measuring sensors and sensor elements have heater units or heat conductors. This also applies, for example, for the planar polarographic probe known from German Published, Non-Examined Patent Application 3,811,713, corresponding to U.S. Pat. No. 5,169,512, which has a pump cell (A) and a diffusion unit (B) having a diffusion resistance upstream of the pumping electrode of the pump cell (A), in which the diffusion resistance of the diffusion unit (B) is formed by a porous, sintered body inserted into the unsintered probe. The layouts of polarographic probes having heater units are shown, for example, in FIGS. 1 and 13 of German Application 3,811,713.

If a planar sensor element comprising a solid substrate has an integrated heat conductor, this conductor is typically embedded in a conventional manner in an insulating material, such as $Al_2O_3$, and the heat conductor and insulating material are in turn embedded in the ion-conductive solid electrolyte material.

The disadvantage of such embedding is the danger of electrical coupling of the heater with the measuring cell(s) integrated into the sensor element. Causes of the above can be:

(1) insufficient thickness of insulation layers between the solid electrolyte and heater;

(2) defective insulating layers due to holes (pinholes), breaches, defective spots;

(3) a limited insulation capacity of the insulating material, and (4) a capacitative influence of the heat conductor on the measuring cell.

SUMMARY OF THE INVENTION

It is an object of the present invention to provide an improved sensor element which has the advantage that the danger of electric coupling of the heater with the measuring cell(s) integrated into the sensor element is eliminated.

The above and other objects are accomplished according to the invention by the provision of one or a plurality of hollow chambers which at least partially separate the two insulating layers in which the heat conductors are embedded from the solid electrolyte substrate of the sensor element. These hollow chambers can be either continuous or non-continuous over the surface of the insulating layers.

The insulating layers preferably extend beyond the region of the hollow chambers, preferably by about 200 μm, while each of the heat conductors lies entirely in the region of one or more hollow chambers associated therewith, preferably also by about 200 μm. The hollow chambers have a thickness of about 2 to about 40 μm, and preferably about 5 to about 20 μm.

The creation of the hollow chambers can be effected in an advantageous manner during production of the sensor elements by means of hollow chamber formers which have hollow chamber layers and which are preferably produced according to conventional methods used in the production of known electrochemical measuring sensors and sensor elements, such as conventional methods used to create diffusion channels. A method of producing a sensor element in which electrodes are exposed by means of hollow chambers is known from, for example, European Patent Application 0,148,622.

Known methods of creating hollow chambers are typically based on a hollow chamber former of a hollow chamber layer being printed onto a film using screen-printing, with the hollow chamber former being made of a combustible, decomposable or vaporizable substance, such as theobromine, indanthrene blue, graphite or carbon black. During production of the sensor element, the hollow chamber(s) is (are) created by means of heating the film laminate to a temperature required for combustion, decomposition or vaporization of the substance used.

The use of graphite or carbon black has proven particularly advantageous in the production of sensor elements according to the invention. Known $O^{2-}$ ion conductive solid electrolyte films formed on a substrate of oxides of quadrivalent metals, particularly $ZrO_2$, $CeO_2$, $HfO_2$ and $Th_2$, which contain bivalent alkaline earth oxides and/or preferably trivalent oxides of the rare earths, are suited for production of the sensor elements according to the invention. In an advantageous manner the solid electrolyte films are made of $Y_2O_3$-stabilized $ZrO_2$. The thickness of the films used is advisably 0.1 to 0.6 mm.

The electrodes, the associated conductor tracks and connections can be printed onto the solid electrolyte films, which are possibly partially provided with an insulating layer, in a conventional manner using known pastes on a precious metal substrate, particularly on a platinum-cermet substrate.

The layout of the hollow chamber layers is preferably configured such that the insulating layers extend into the solid electrolyte substrate beyond the region of the hollow chambers created from the hollow chamber layers, but each of the heat conductors lies entirely in the region of one or more hollow chambers associated therewith. The through-contact region of the heat conductor is advantageously stamped out from the hollow chamber construction.

A typical paste for printing a hollow chamber layer has the following composition:

| | |
|---|---|
| graphite or carbon black | 36.0 weight-% |
| binding agent (e.g. polyvinyl butyral) | 8.0 weight-% |
| plasticizing agent (e.g. dioctylphthalate) | 4.0 weight-% |
| solvent | 52.0 weight-% |

BRIEF DESCRIPTION OF THE DRAWINGS

The foregoing objects of the invention, together with other objects and advantages which may be attained by its use, will become more apparent upon reading the following detailed description of the invention taken in conjunction with the drawings. In the drawings, wherein the reference numerals identify corresponding components.

DETAILED DESCRIPTION OF THE PREFERRED EMBODIMENTS

Figure 1:
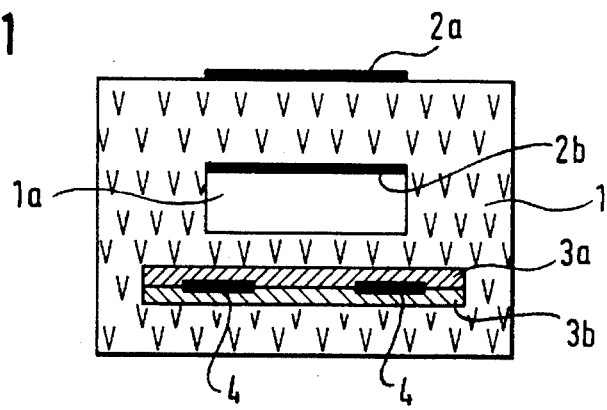
FIG. 1 shows a cross-sectional view of a planar sensor element having an integrated heat conductor according to the prior art.

The planar sensor element of the prior art illustrated in FIG. 1 comprises a solid electrolyte substrate 1 formed from ion-conductive solid electrolyte films, an electrode pair 2a, 2b, which forms the measuring cell, and a heat conductor 4 embedded in insulating layers 3a, 3b and made of, for example, platinum. A reference channel 1a lies within solid electrolyte substrate 1.

In the conventional sensor element according to FIG. 1, the operative insulation segment between the heat conductor and the solid electrolyte is the layer thickness of the insulation (20 to 30 μm). If defects, such as holes or breaches, are present in these layers, the heater couples electrically with the measuring cell; such coupling can lead to a falsification of the electrical signals associated with the sensor. The above is especially true for the insulating layer located above the heat conductor, because solid electrolyte paste is typically applied to this layer.

Figure 2:
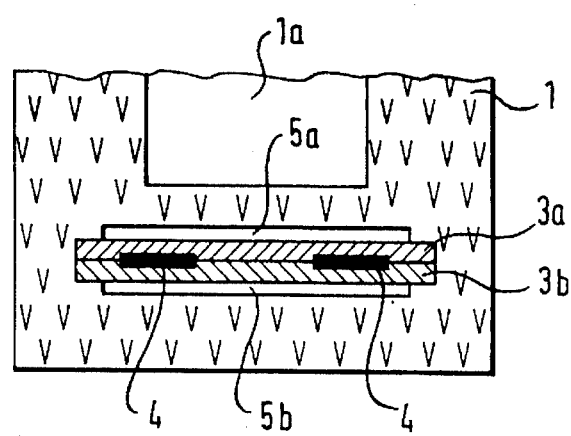
FIGS. 2–4 each show a partial cross-sectional view of different embodiments of heat conductor units of planar sensor elements having an integrated heat conductor according to the invention.
Figure 3:
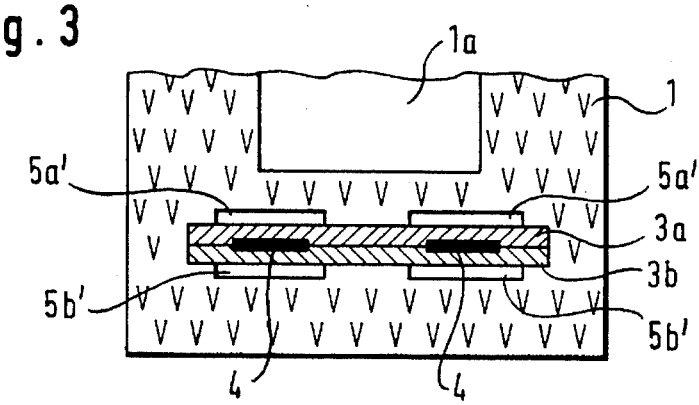
Figure 4:
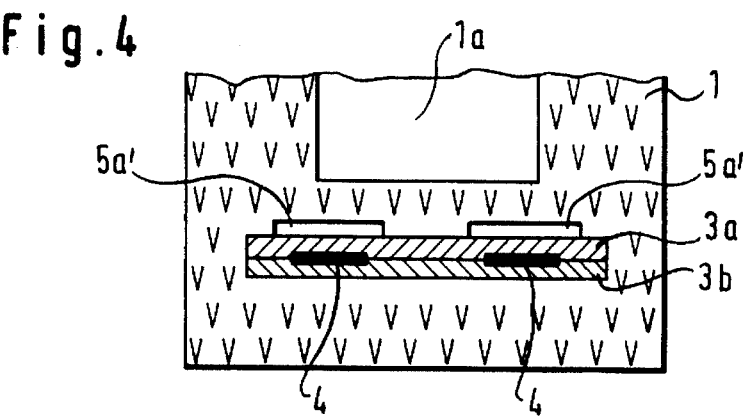

The embodiments illustrated in FIGS. 2–4 of heat conductor units of sensor elements according to the invention differ from the corresponding production units of known sensor elements such as the element according to FIG. 1 by virtue of the presence of hollow chambers. Only the heat conductor units of sensor elements according to the invention are illustrated in FIGS. 2–4, because the measuring cell(s) can have an arbitrary, known structure. According to a particularly advantageous embodiment of the invention, the heat conductor unit illustrated in FIGS. 2–4 can be combined with, for example, a pump cell, a diffusion unit and possibly a Nernst cell according to German Application 3,811,713, to form a planar polarographic sensor element or a planar polarographic probe.

An essentially improved decoupling of the heat conductor from the measuring cell is achieved by the presence of hollow chambers because:

(1) an essentially thicker insulating segment (approximately 200 μm) is created by the presence of the chambers between the heat conductor and the solid electrolyte; and (2) the hollow chambers ensure that no direct contact is effected between the heat conductor and the solid electrolyte by means of hole and breach formation. The hollow chamber on the upper insulation layer particularly prevents contact by way of the printed solid electrolyte paste.

In the case of the heat conductor unit illustrated in FIG. 2, the two insulating layers 3a and 3b are located adjacent hollow chambers 5a and 5b, respectively, the chambers being continuous over the outer surface of each of the insulating layers 3a and 3b.

In the case of the heat conductor unit illustrated in FIG. 3, the two insulating layers 3a and 3b are each covered by two hollow chambers 5a' and placed on top of two hollow chambers 5b', the chambers thus being noncontinuous over the outer surface of each of the insulating layers 3a and 3b. By means of the above structure, a buttressing effect is achieved for the electrolyte substrate, and at the same time the heat conduction between the heat conductor and the measuring cell is improved.

FIG. 4 shows an embodiment of a heat conductor unit in which two hollow chambers 5a' are provided only on one side of the insulating layers, namely on one side of layer 3a. Advantages of these embodiments include an improvement in heat conduction to the measuring cell and a higher inherent stability of the heater system.

Figure 5:
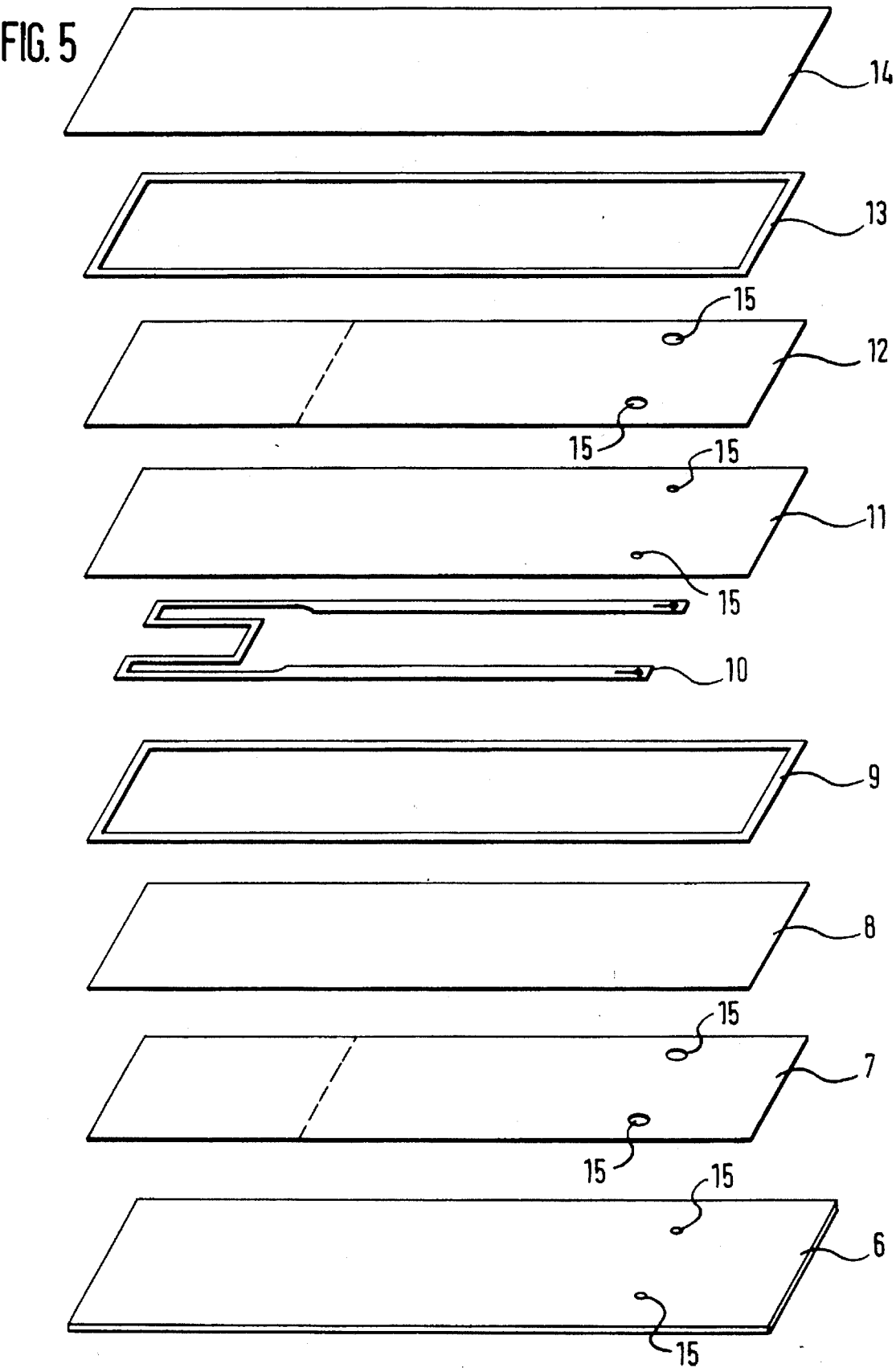
FIG. 5 shows an exploded view of a heat conductor unit of a planar sensor element according to the invention.

FIG. 5 is an exploded view which more clearly depicts the layered structure of the heat conductor unit according to the invention. As suggested in FIG. 5, the production of a heat conductor unit according to the invention in the embodiments shown in cross-section in FIGS. 2 and 3 is effected by assembling the following elements: the ion-conductive solid electrolyte film 6, for example of $ZrO_2/Y_2O_3$; hollow chamber layer 7, which may be noncontinuous and which forms one or a plurality of hollow chambers; insulating layer 8; sealing frame 9; heater 10; insulating layer 11; hollow chamber layer 12, which may also be noncontinuous and which forms one or a plurality of hollow chambers; sealing frame 13; and a layer 14 of a solid electrolyte paste, which connects the heat conductor unit with at least one measuring cell, not shown, of a conventional design. The solid electrolyte film 6, hollow chamber layers 7 and 12 and insulating layer 11 have conventional through-contacts 15. Laminating the films, printing and further processing the laminate, including creating the hollow chambers from the hollow chamber layers, are executed according to known techniques as discussed above.

The production of a sensor element according to the invention can therefore be effected in an advantageous manner, for example according the method described in German Application 3,811,713.

The foregoing is a complete description of the present invention. Various changes may be made without departing from the spirit of the present invention. The invention, therefore, should be limited only by the scope of the claims which follow.

What is claimed is:

1. In a planar sensor element for determining the oxygen content of a gas mixture and including a solid electrolyte substrate, and measuring cells and a heater unit integrated into the substrate, the heater unit including electric insulation material and a heat conductor embedded in the electric insulation material, the improvement wherein at least one part of the electric insulation material in which the heat conductor is embedded is separated from the solid electrolyte substrate of the sensor element by at least one hollow chamber which is not in communication with the gas mixture and the measuring cells thereby providing added electrical insulation between the heater unit and the measuring cells.

2. The planar sensor element according to claim 1, wherein said insulation material comprises two insulating layers between which said heat conductor is embedded.

3. The planar sensor element according to claim 2, wherein said at least one hollow chamber comprises a continuous hollow chamber separating at least one of said two insulating layers from said solid electrolyte substrate.

4. The planar sensor element according to claim 2, wherein said at least one hollow chamber comprises a noncontinuous hollow chamber separating at least one of said two insulating layers from said solid electrolyte substrate.

5. The planar sensor element according to claim 1, wherein said insulation material extends beyond a region defined by said at least one hollow chamber by about 200 µm.

6. The planar sensor element according to claim 1, wherein said heat conductor extends entirely within said region.

7. The planar sensor element according to claim 6, wherein the region of said at least one hollow chamber extends beyond said heat conductor by a total of about 200 µm.

8. The planar sensor element according to claim 1, wherein said at least one hollow chamber has a thickness of at least 2 µm.

9. The planar sensor element according to claim 1, wherein said at least one hollow chamber has a thickness of at least 5 µm.

10. The planar sensor element according to claim 1 and further including through-contacts connected to said heat conductor and being exposed by said at least one hollow chamber.

* * * * *